United States Patent [19]

Kramer et al.

[11] Patent Number: 4,861,885

[45] Date of Patent: Aug. 29, 1989

[54] ALLYLBICYCLO[2.2.1]HEPT-5-ENE-2-CARBOXYLIC ACID AMIDES

[75] Inventors: Andreas Kramer, Düdingen; Roland Darms, Therwil, both of Switzerland

[73] Assignee: Ciba-Geigy Corporation, Ardsley, N.Y.

[21] Appl. No.: 939,216

[22] Filed: Dec. 8, 1986

[30] Foreign Application Priority Data

Dec. 16, 1985 [CH] Switzerland .................. 5340/85

[51] Int. Cl.⁴ .................. A61K 7/22; A61K 31/19; A61K 31/44; C07C 59/48; C07C 103/19; C07D 31/44; C07D 209/94
[52] U.S. Cl. .................. 544/387; 564/123; 564/152; 564/153; 564/155; 564/191; 424/48; 426/638; 549/450; 558/303; 558/432; 560/128; 568/446; 562/867
[58] Field of Search .............. 564/123, 191, 152, 153, 564/155; 544/387

[56] References Cited

U.S. PATENT DOCUMENTS

| | | | |
|---|---|---|---|
| 2,975,125 | 3/1961 | Batzer et al. | 564/152 X |
| 3,068,284 | 12/1962 | Nordstrom, II | 534/152 X |
| 3,130,227 | 4/1964 | Takahashi et al. | 564/152 |
| 3,287,395 | 11/1966 | Chang | 260/468 |
| 3,658,669 | 4/1972 | Colomb, Jr. et al. | 204/59.12 |
| 3,673,197 | 6/1972 | Rynbrandt | 564/155 X |
| 3,789,042 | 1/1974 | Colomb, Jr. et al. | 260/17.4 |
| 3,941,836 | 3/1976 | Coleman | 260/557 R |
| 3,966,797 | 6/1976 | Colomb, Jr. et al. | 260/484 A |
| 4,331,570 | 5/1982 | Klemarczyk et al. | 252/522 R |
| 4,515,962 | 5/1985 | Renner | 548/435 |
| 4,622,339 | 11/1986 | Lieb et al. | 514/563 |

FOREIGN PATENT DOCUMENTS 257569 10/1967 Austria .................. 564/152

OTHER PUBLICATIONS

Nordstroms, Chemical Abstracts, vol. 59, #7392e, (1963).
Renner, Chemical Abstracts, vol. 101, #131730q, (1984).
Tetrahedron Letters, 25, 2697-2700, (1984), Gonzalez et al.

Primary Examiner—Floyd D. Higel
Attorney, Agent, or Firm—Harry Falber

[57] ABSTRACT

The present invention relates to amides of formula I

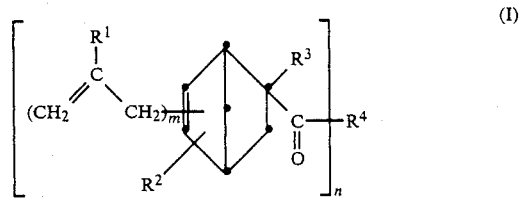

wherein $R^1$, $R^2$ and $R^3$ are independently hydrogen or methyl, m is 1 to 5 and n is 1 to 5 and $R^4$ is —$NH_2$ or is derived from a mono- to pentavalent amine.

Intermediates of formula VIII

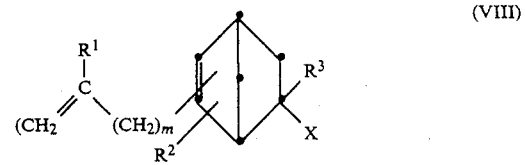

wherein $R^1$, $R^2$, $R^3$ and m are as defined above and X is a carboxylic acid or acid ester group, —COCl, —COBr, —CHO or —CN, are also described.

The compounds of formula I can be polymerized thermally. They are suitable for the preparation of adhesives, matrix resins or electrical insulating materials.

7 Claims, No Drawings

ALLYLBICYCLO[2.2.1]HEPT-5-ENE-2-CARBOXYLIC ACID AMIDES

The present invention relates to novel allylbicyclo[2.2.1]hept-5-ene-2-carboxylic acids and derivatives thereof, in particular the carboxamides, to a process for the preparation of the carboxamides, to polymers which are derived from these carboxamides, and also to the use of the carboxamides for the preparation of cured products.

Derivatives of allylbicyclo[2.2.1]hept-5-ene-2,3-dicarboxylic acid are known. Published European patent application 105 024 describes imides of said dicarboxylic acid and also the polymers which can be obtained by thermal polymerisation of the monomers. The polymeric products are suitable e.g. as matrix resins for composite materials or as insulating materials.

Derivatives of allylbicyclo[2.2.1]hept-5-ene-2-carboxylic acid have been described by A. G. Gonzalez et al. in Tetrahedron Lett. 25(25), pp. 2697-2700 (1984). In addition to carrying the allyl function and the carboxylic acid function, these compounds also carry a hydroxyl group in the 7-position. This treatise relates to the synthesis of stereospecific functionalised derivatives of the bicyclo[2.2.1]heptene system. No mention is made of the appicability of these compounds or of the further processing thereof to polymers.

The present invention relates to compounds of formula I

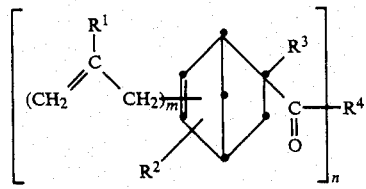

(I)

wherein
$R^1$, $R^2$ and $R^3$ are each independently hydrogen or methyl,
m is an integer from 1 to 5,
n is an integer from 1 to 5, and
$R^4$ is —$NH_2$ or an n-valent radical of a primary and/or secondary aliphatic, cycloaliphatic, aromatic, araliphatic or heterocyclic (poly)amine after removal of n active hydrogen atoms bonded to amino nitrogen atoms, which radical is attached to the respective carbonyl radicals through the amino groups.
$R^4$ is —$NH_2$ or a mono- to pentavalent radical which is derived from (poly)amines containing one to five secondary and/or primary amino groups.

These amino groups may be part of an aliphatic or heterocyclic system or they are attached as substituents to a mono- to pentavalent radical.

Examples of amines of the last-mentioned type are compounds of formula II

(II)

wherein n is an integer from 1 to 5, $R^5$ is hydrogen, $C_1$–$C_{20}$alkyl, $C_3$–$C_{12}$alkenylmethyl, $C_3$–$C_{12}$alkynylmethyl, $C_3$–$C_{12}$cycloalkyl, phenyl, naphthyl, $C_7$–$C_9$aralkyl or $C_7$–$C_9$alkaryl and $R_6$ is an n-valent aliphatic, cycloaliphatic, aromatic, araliphatic or heterocyclic radical, with the proviso that the individual radicals $R^5$ of a molecule may, within the definitions indicated, differ in meaning from one another.

$R^5$ as $C_1$–$C_{20}$alkyl is a radical with a straight or branched, preferably straight, alkyl chain. Examples of such radicals are methyl, ethyl, n-propyl, isopropyl, n-butyl, sec-butyl, pentyl, hexyl, 2-ethylhexyl, octyl, decyl, dodecyl, tetradecyl, hexdecyl, octadecyl or eicosyl.

$R^5$ may also be substituted alkyl. Examples of substituents are $C_1$–$C_4$alkoxy, halogen, preferably chlorine or bromine, or cyano.

$R^5$ as alkyl is preferably $C_1$–$C_8$alkyl, most preferably methyl.

$R^5$ as $C_3$–$C_{12}$cycloalkyl is for example cyclopropyl, cyclobutyl, cyclopentyl, cyclohexyl, cycloheptyl, cyclooctyl, cyclodecyl or cyclododecyl, with cyclohexyl being particularly preferred.

$R^5$ as $C_3$–$C_{12}$alkenylmethyl is for example prop-2-enyl, but-3-enyl, hex-5-enyl, oct-7-enyl, dec-9-enyl or dodec-11-enyl, with prop-2-enyl being particularly preferred.

$R^5$ as $C_3$–$C_{12}$alkynylmethyl is for example prop-2-ynyl, but-3-ynyl, hex-5-ynyl, oct-7-ynyl, dec-9-ynyl or dodec-11-ynyl, with propargyl being particularly preferred.

$R^5$ as $C_7$–$C_9$aralkyl is for example benzyl, α-methylbenzyl or α,α-dimethylbenzyl, with benzyl being preferred.

$R^5$ as $C_7$–$C_9$alkaryl is preferably tolyl or xylyl, with tolyl being preferred.

$R^4$ is preferably the radical of a primary or secondary monoamine of formula II, in which case $R^6$ has for example one of the meanings defined for $R^5$ or is a 5- or 6-membered heterocyclic radical cotaining one to three oxygen, sulfur and/or nitrogen atoms.

Examples of such heterocyclic radicals are furan-2-yl, thiophen-2-yl, pyrrol-2-yl, pyridin-2-yl, 2-H-pyran-3-yl, imidazol-2-yl, pyrazol-3-yl, pyrazin-2-yl, pyrimidin-4-yl, pyrazin-4-yl, isothiazol-3-yl, isoxazol-3-yl, furazan-3-yl, pyrrolin-2-yl, pyrrolidin-2-yl, imidazolin-2-yl, pyrazolidin-3-yl, piperidin-2-yl, piperazin-2-yl or morpholin-2-yl, with furan-2-yl being particularly preferred.

$R^4$ is preferably derived from a diprimary diamine or from a secondary-primary diamine of formula II.

$R^6$ is then for example a $C_2$–$C_{18}$alkylene which may be interrupted by individual oxygen atoms.

Examples of such radicals are ethylene, trimethylene, tetramethylene, pentamethylene, hexamethylene, heptamethylene, octamethylene, decamethylene, dodecamethylene, tetradecamethylene, hexadecamethylene, octadecamethylene or radicals of the formula —($CH_2$—$CH_2$—O)$_s$—$CH_2CH_2$—, wherein s is an integer from 1 to 8.

If $R^4$ is derived from a cycloaliphatic diamine, then $R^4$ is preferably a derivative of cyclopentanediamine, cyclohexanediamine or bis(aminocyclohexyl)methane. The rings may be substituted by one to three alkyl groups, preferably methyl. Examples of divalent cycloaliphatic radicals $R^6$ in the amine of formula II are cyclopent-1,4-diyl, cyclopent-1,3-diyl, cyclohex-1,2-diyl, cyclohex-1,3-diyl, cyclohex-1,4-diyl, dicyclohexylmethane-3,3'-diyl, dicyclohexylmethane-3,4'-diyl, dicyclohexylmethane-4,4'-diyl or di-3,3'-dimethylcyclohexylmethane-4,4'-diyl. Further divalent cycloaliphatic radicals $R^4$ are derived from isophoronediamine, 1,3- and 1,4-(aminomethyl)cyclohexane or 3(4),8(9)-bis-(aminomethyl)tricyclo[5.2.1.0$^{2,6}$]decane.

If $R^4$ is derived from an araliphatic diamine, then said diamine is for example an amine of formula II, wherein $R^6$ is 1,3- or 1,4-xylylene.

$R^4$ may also be derived from a aromatic diamine. In this case $R^4$ is a radical containing at least one aromatic ring. Several aromatic nuclei may be fused to one another or they may be linked to one another through a bridge member.

Examples of divalent aromatic radicals $R^6$ in the amine of formula II are 1,3-phenylene, 1,4-phenylene, 2,4-tolylene, 4,4'-diphenylmethane, 4,4'-diphenyl ether, 4,4'-diphenylsulfone, 4,4'-diphenyl ketone, 4,4'-diphenyl sulfide, 4,4'-diphenyl and the corresponding 3,3'- or 3,4'-derivatives.

$R^4$ may also be derived from a divalent heterocyclic diamine. Examples of such diamines are 2,4- or 2,6-diaminopyridine or 2,4-diaminopyrimidine, N,N'-bis(3-aminopropyl)piperazine or 2,4-diamino-s-triazine.

If the amino groups of the radical $R^4$ are part of a heterocyclic system, then said diamine is for example a piperazine, or 2-methylpiperazine or also N-aminoethylpiperazine.

Examples of amines containing three to five amino groups, from which amines $R^4$ is derived, are aliphatic polyamines of the formula $H_2N-(CH_2-CH_2-NH)_t-CH_2-CH_2-NH_2$ (t=1 to 3), 2,4,6-triaminocyclohexane, 2,4,6-triaminobenzene, 2,4,6-triaminomethylbenzene or 2,4,6-triamino-s-triazine.

Preferred compounds of formula I are those wherein $R^1$, $R^2$ and $R^3$ are hydrogen. The index m is preferably 1 or 2. Compounds of formula I wherein n is an integer from 2 to 5 are also preferred.

Particularly preferred compounds of formula I are those wherein n is an integer from 2 to 5, and $R^4$ is derived from α,ω-alkylenediamines, m- or p-phenylenediamine, m- or p-xylylenediamine, or from compounds of formulae III, IV, V, VI or VII

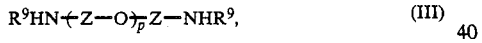

(III)

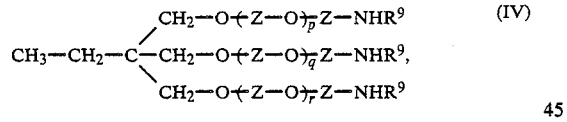

(IV)

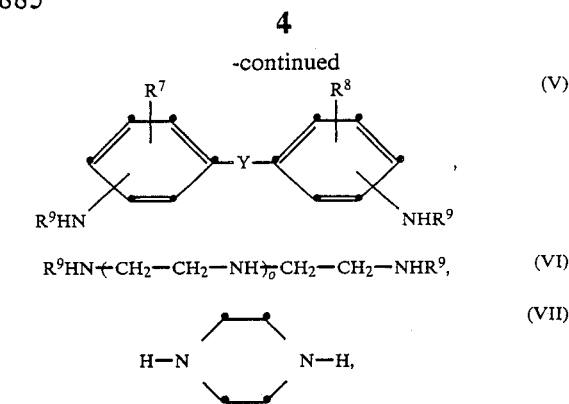

(V)

$R^9HN+CH_2-CH_2-NH)_oCH_2-CH_2-NHR^9$, (VI)

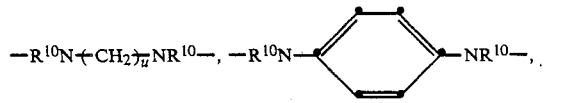

(VII)

in which formulae the bridge Y is a direct C—C bond, or —O—, —S—, —SO$_2$—, —CO—, —CH$_2$— or C(CH$_3$)$_2$—, $R^7$, $R^8$ and $R^9$ are each independently hydrogen or C$_1$-C$_5$alkyl, Z is one of the radicals —CH$_2$—CH$_2$—, —CH$_2$—CH$_2$—CH$_2$— or —CH$_2$—CH(CH$_3$)—, the indexs o is an integer from 0 to 2 and the indices p, q and r are each independently integers from 1 to 8.

Further particularly preferred compounds of formula I are those wherein m is 1 or 2 and n is 2, $R^4$ is selected from the group consisting of

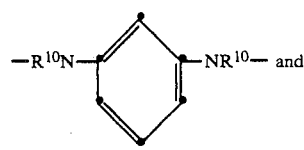

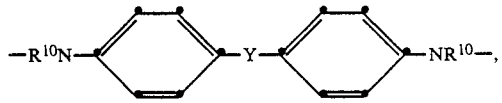

in which formulae Y is —O—, —SO$_2$—, —CO— or —CH$_2$—, $R^{10}$ is hydrogen, C$_1$-C$_5$alkyl or phenyl and u is an integer from 2 to 12.

Compounds of formula I of particular interest are those wherein $R^1$ and $R^2$ are hydrogen and $R^3$ is methyl.

Most particularly preferred compounds are

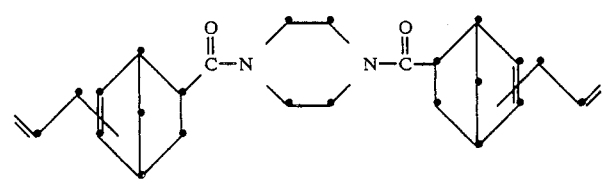

and

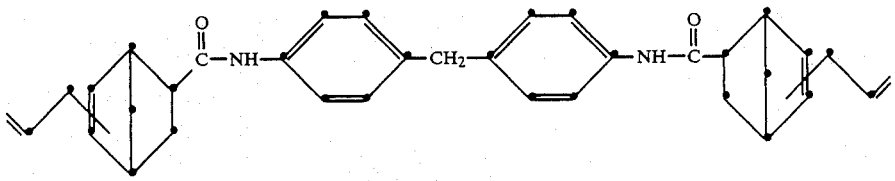

Compounds of formula I which are also preferred are those wherein m is 1 or 2, n is 1, $R^4$ is $-NR^{12}R^{13}$ and $R^{12}$ and $R^{13}$ are each independently of the other hydrogen, $C_1$-$C_8$alkyl, allyl, cyclohexyl, phenyl, benzyl or tolyl.

The compounds of formula I can be obtained in a manner known per se by amidation of the carboxylic acids, carboxylic acid esters or carboxylic acid halides of formula VIII. The intermediates of formula VIII are novel and likewise constitute an object of the present invention.

Accordingly, the present invention also relates to compounds of the formula VIII

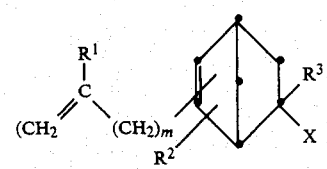

(VIII)

wherein
$R^1$, $R^2$ and $R^3$ are each independently hydrogen or methyl,
X is $-COOH$, $-COOR^{11}$, $-COCl$, $-COBr$, $-CHO$ or $-CN$,
$R^{11}$ is $C_1$-$C_{20}$alkyl, $C_3$-$C_{12}$alkenylmethyl, $C_3$-$C_{12}$alkynylmethyl, $C_3$-$C_{12}$cycloalkyl, phenyl, naphthyl, $C_7$-$C_9$aralkyl, $C_7$-$C_9$alkaryl or a 5- or 6-membered heterocyclic ring containing one to three oxygen, sulfur and/or nitrogen atoms and
m is an integer from 1 to 5.

$R^{11}$ as $C_1$-$C_{20}$alkyl, $C_3$-$C_{12}$alkenylmethyl, $C_3$-$C_{12}$alkynylmethyl, $C_3$-$C_{12}$cycloalkyl, $C_7$-$C_9$aralkyl or $C_7$-$C_9$alkaryl is, as a rule, one of the radicals as defined above for the corresponding meanings of $R^5$.

$R^{11}$ as a 5- or 6-membered heterocyclic ring containing one to three oxygen, sulfur and/or nitrogen atoms is one of the aromatic or non-aromatic radicals as defined above for the corresponding meanings of $R^6$.

Particularly preferred compounds of formula VIII are those wherein X is $-COOH$, $-COOR^{11}$ or $-COCl$, $R^{11}$ is $C_1$-$C_8$alkyl, allyl, cyclohexyl, phenyl, benzyl, tolyl or furan-2-yl and m is 1 or 2.

Most particularly preferred compounds of formula VIII are those wherein $R^1$, $R^2$ and $R^3$ are hydrogen, X is one of the radicals $-COOH$, $-COOCH_3$, $-COOC_6H_5$ or $-COCl$ and m is 1 or 2.

The compounds of formula VIII can be prepared by a process analogous to that which is known from U.S. Pat. No. 3,105,839. In this process, first cyclopentadiene or methylcyclopentadiene is reacted with an allyl halide in accordance with the following scheme. The reaction product is then reacted with an acrylic or methacrylic acid derivative in a Diels-Alder reaction to give a compound of formula VIII.

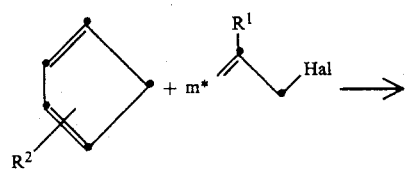

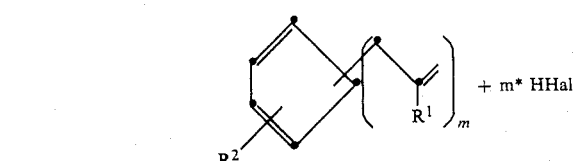

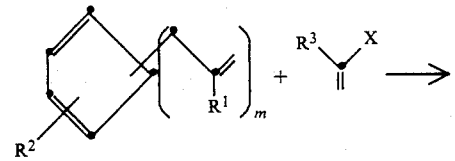

(VIII)

In this scheme, $R^1$, $R^2$, $R^3$, X and m are as defined above. An allyl halide suitable for use is for example the chloride or bromide, the chloride being preferred.

It is preferred to use as acrylic or methacrylic acid derivative the acid chloride or the ester, the methyl ester being preferred.

The compounds of formula I can be prepared in a manner known per se, e.g. by reacting a carboxylic acid, a carboxylic acid ester or a carboxylic acid chloride or bromide of formula VIII with ammonia or with a (poly)amine containing primary and/or secondary amino groups, for example with an amine of the above-defined formula II.

Primary or secondary amines may be employed for the reaction with the carboxylic acid chlorides and bromides of formula VIII, whereas the esters of formula VIII can usually only be reacted with primary amines.

If the reaction is carried out with an acid chloride or bromide, then, as a rule, the ammonia or the amine is employed in stoichiometric amounts, based on the amino groups. The hydrogen chloride or bromide evolving is neutralised by the addition of stoichiometric amounts of a base, preferably a tertiary amine, e.g. triethylamine or pyridine, or by using an excess of ammonia or primary or secondary amine.

If N-substituted amides of formula I are desired, then secondary amines are reacted as described above with the acid chloride or bromide of formula VIII.

The reaction of the ester of formula VIII is usually effected at elevated temperatures, preferably in the range from 120° to 160° C., with an excess of primary amine of formula II and in the presence of a basic catalyst such as an alkali metal alcoholate, preferably sodium methanolate, or an alkalie metal hydroxide.

If the ester of formula VIII is reacted with benzylamine, ammonium chloride can also be used as catalyst.

Accordingly, the invention also relates to a process for the preparation of compounds of formula I by reacting a carboxylic acid chloride of formula IX

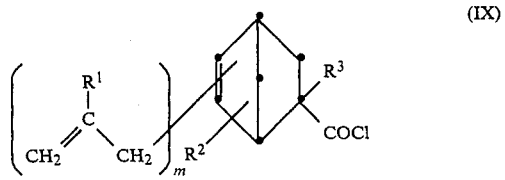

(IX)

wherein $R^1$, $R^2$ and $R^3$ are each independently hydrogen or methyl and m is an integer from 1 to 5, with a primary and/or secondary aliphatic, cycloaliphatic, aromatic, araliphatic or heterocyclic (poly)amine containing one to five amino groups, which amino groups of the (poly)amine must be present in an amount at least equivalent to the amount of carboxylic acid chloride, in the presence of a tertieary amine in an amount at least equivalent to the amount of carboxylic acid chloride, or by reacting a carboxylic acid chloride of formula IX as defined above with at least twice the equivalent amount of amino groups of a (poly)amine as defined above.

The invention further relates to a process for the preparation of compounds of formula I containing an aliphatic, cycloaliphatic or araliphatic radicval $R^4$ by reacting a carboxylic acid ester of formula X

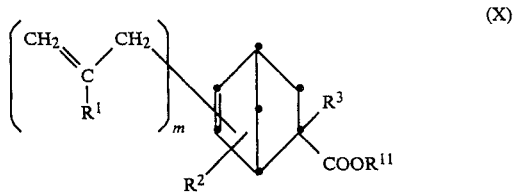

(X)

wherein $R^1$, $R^2$, $R_3$, $R^{11}$ and m are as defined above, with a primary aliphatic, cycloaliphatic or araliphatic (poly)amine containing one to five amino groups, which amino groups of the (poly)amine are present in about 1.1 to 2.0 times the molar amount, based on the amount of the carboxylic acid ester of formula X, in the presence of a basic catalyst and in the temperature range from 120° to 160° C.

The reactions may be effected without a solvent or in the presence of an inert solvent. Examples of solvents are hydrocarbons or chlorinated hydrocarbons such as petroleum ether, dichloromethane, chloroform, benzene, toluene, xylene or chlorobenzene, and also ethers such as diethyl ether or dioxane.

Further intermediates of formula VIII (aldehydes, nitriles) may be converted in known manner via intermediary steps into carboxylic acid chlorides, bromides or esters and then further processed to corresponding amides of formula I.

The amides of formula I of the invention are liquid or low melting solid substances which are, as a rule, readily soluble in organic solvents and which can be polymerised to solid insoluble products which have a high glass transition temperature and are strongly resistant to heat and water. The polymerisation of the monoamides of formula I usually only yields oligomeric products which are soluble in organic solvents.

However, the monoamides of formula I can be employed together with the other amides of formula I as polymerisable solvents. Particularly suitable monoamides are those containing ethylenically unsaturated N-substituents, e.g. N-allylmonoamides or N,N-diallylmonoamides. The addition of monoamides of formula I to the higher amides of formula I has an influence on the viscosity of the mixture of monomers.

The monomers of formula I (which may be employed in admixture with monoamides of formula I) can be polymerised direct, or they may first be dissolved in an organic solvent such as toluene, xylene, methyl ethyl ketone, glycol ether, acetone or dichloromethane. The resultant solution may be employed as an impregnatinng or coating agent or it may also be dispatched to the end user. Impregnation with the monomers of formula I may also be effected with advantage from the melt.

Compared with corresponding imides, the monomeric amides of formula I of the invention are distinguished by a surprisingly high reactivity. Accordingly, a thermal polymerisation can even be performed at temperature from 150° C. Moreover, no volatile components are formed during polymerisation, which is an advantage in many areas of application, e.g. in the preparation of varnish films or with respect to the use as matrix resins.

Accordingly, the invention also relates to polymers which can be obtained by heating a compound of formula I, in particular those in which n is 2 to 5, or a mixture of such compounds for 6 to 60 hours, preferably 6 to 24 hours, at a temperature in the range from 150° to 300° C., preferably from 150° to 220° C., most preferably from 160° to 220° C.

Inert and stable substances such as fillers, pigments, dyes and other customary additives may, of course, be added to the monomeric compounds before they are polymerised to crosslinked structures.

The compounds of formula I may be employed in a large variety of ways, e.g. as casting resins or for the preparation of heat-resistant adhesives, of electrical insulating materials or also, in particular, of matrix resins for fibre-reinforced composite materials. Suitable reinforcing agents are, in particular, glass, carbon and polyamide fibres.

The invention also relates to the use of the compounds of formula I for the preparation of cured products.

EXAMPLE 1: Preparation of allylbicyclo[2.2.1]hept-5-ene-2-carbonyl chloride

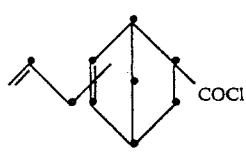

A solution of 400 g of NaOH in 800 ml of H₂O and 16 g of benzyltriethylammonium chloride (dissolved in 32 ml of ethanol) is heated to 30°-35° C., and 264 g of cyclopentadiene is then added, with stirring, over 15 minutes. 336 g of allyl chloride are aded over 45 minutes to the deep red clear emulsion, directly initiating a reaction which is discernible by the evolution of heat and the precipitation of sodium chloride. The temperature of the reaction mixture is kept in the range from 50° to 55° C. by means of an ice bath. When the dropwise addition of the allyl chloride is complete, stirring is continued for a further 30 minutes at 50° C. The reaction solution is cooled, and 200 ml of water are added, whereupon the precipitated salt goes into solution. The aqueous phase is separated, and the organic phase is washed twice with saturated NaCl solution and filtered over sodium sulfate. The unreacted cyclopentadiene and allyl chloride are distilled off at room temperature and under reduced pressure. This purification operation is discontinued as soon as an absolute pressure of 25 mm has been reached. Chromatographic analysis of the residue shows that, in addition to allylcyclopentadiene (about 75%), there are also present as by-products di- and triallylcyclopentadiene, dicyclopentadiene and diallyldicyclopentadiene. 360 g of crude allylcyclopentadiene are taken up in 400 ml of methylene chloride. With ice cooling, 252 g of acryloyl chloride are added dropwise at 20°-25° C. to the resultant clear reddish brown solution over 1 hour, and stirring is subsequently effected for 2 hours at 20° C. The reaction solution is concentrated by rotary evaporation, and the residue is distilled at an absolute pressure of 20 mm. In the temperature range from 112° to 120° C., 377 g of allylbicyclo[2.2.1]hept-5-ene-2-carbonyl chloride distill, which corresponds to a yield of 68% of theory. The yellow liquid can be stored under nitrogen over a prolonged period at 0° C. The acid chloride is converted into the corresponding methyl ester for the purpose of characterisation. The gas chromatographic data correspond with those for the methyl ester prepared by the procedure of Example 5.

| Analysis (methyl ester) | | |
|---|---|---|
| | % C | % H |
| calculated for C₁₂H₁₆O₂ | 74.97 | 8.39 |
| found | 73.95 | 8.35 |

EXAMPLE 2: Preparation of allylbicyclo[2.2.1]hept-5-ene-2-methyl-2-carbonyl chloride

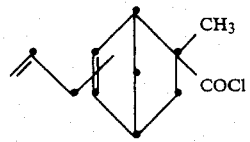

By using the corresponding methacryl compound instead of the acryl compound employed in Example 1 and otherwise following the procedure described in Example 1, the above-mentioned acid chloride is obtained. The compound is characterised via the methyl ester (Example 6).

EXAMPLE 3: Preparation of methallylmethylbicyclo[2.2.1]hept-5-ene-2-carbonyl chloride and methyl methallylmethylbicyclo[2.2.1]hept-5-ene-2-carboxylate

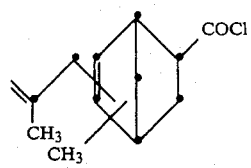
(a)

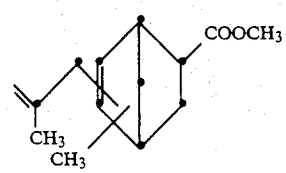
(b)

(a) By replacing cyclopentadiene and allyl chloride by methylcyclopentadiene and methallyl chloride and otherwise repeating the procedure described in Example 1, the above-mentioned acid chloride is obtained.

The acid chloride is converted into the methyl ester for the purpose of characterisation and then compared with the product obtained by synthesis route (b). With respect to their gas chromatographic data, both compounds correspond with each other.

(b) Over 20 minutes, a solution of 12 g of methyl acrylate in 50 ml of ether is added dropwise to a solution of 24.6 g of methallylmethylcyclopentadiene, prepared from methallyl chloride and methylcyclopentadiene inn accordance with the procedure of Example 1, in 100 ml of ether. The clear reaction solution is boiled under reflux overnight. The ether is distilled off, and the residue is fractionated through a column. At a pressure of 20 mm and in the temperature range from 122° to 127° C., 13.5 g (51% of theory) of ester distill in the form of a faintly yellow liquid; $n_D^{20} = 1.4843$.

| | Analysis | |
|---|---|---|
| | % C | % H |
| calculated for C₁₄H₂₀O₂ | 76.33 | 9.15 |
| found | 76.91 | 9.20 |

EXAMPLE 4: Preparation of diallylbicyclo[2.2.1]hept-5-ene-2-carbonyl chloride

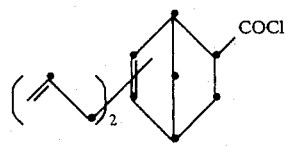

Under the same reaction conditions as in Example 1, 132 g of cyclopentadiene and 321 g of allyl chloride are added dropwise to 300 g of NaOH in 600 ml of H₂O and 12 g of benzyltriethylammonium chloride (dissolved in 24 ml of ethanol). Afterr the dropwise addition, stirring is effected for 2 hours at 65° C. The salt formed is dissolved by the addition of water, and the phase are separated. The organic phase is washed twice with saturated NaCl solution and filtered over sodium sulfate. Vacuum distillation of the reddish brown filtrate affords 135 g of diallylcyclopentadiene; b.p.: 70°–82° C. at 20 mm.

| Analysis (diallylcyclopentadiene) | % C | % H |
|---|---|---|
| calculated for C₁₁H₁₄ | 90.35 | 9.65 |
| found | 90.18 | 9.61 |

81 g of diallylcyclopentadiene are dissolved in 200 ml of methylene chloride. With ice cooling, 45 g of acryloyl chloride are added dropwise over 30 minutes at 20° C. to this solution, and stirring is subsequently effected for 1 hour at room temperature. Distillation of the reaction product affords 84.4 g (73% of theory) of diallylbicyclo[2.2.1]hept-5-ene-2-carbonyl chloride; b.p.: 125°–134° C. at 20 mm.

| Analysis | % Cl |
|---|---|
| calculated for C₁₄H₁₇OCl | 14.98 |
| found | 14.10 |

EXAMPLE 5: Preparation of methyl allylbicyclo[2.2.1]hept-5-ene-2-carboxylate

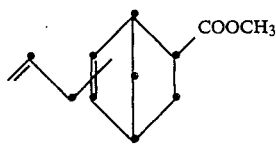

137 g of methyl acrylate are added dropwise over 30 minutes to a solution of 170 g of allylcyclopentadiene, prepared in accordance with the procedure of Example 1, in 200 ml of ether. The clear solution is boiled under reflux for 2 hours. The ether is distilled off, and the residue is fractionated in vacuo through a column. At a pressure of 20 mm and in the temperature range from 107° to 115° C., 163 g of methyl allylbicyclo[2.2.1]hept-5-ene-2-carboxylate distill in the form of a faintly yellow liquid; $n_D^{20} = 1.4863$.

| Analysis | % C | % H |
|---|---|---|
| calculated for C₁₂H₁₆O₂ | 74.97 | 8.39 |
| found | 74.93 | 8.38 |

EXAMPLE 6: Preparation of methyl allylbicyclo[2.2.1]hept-5-ene-2-methyl-2-carboxylate

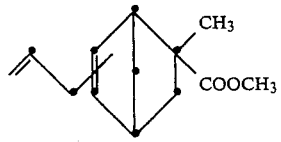

By using the corresponding methacryl compound instead of the acryl compound employed in Example 5 and otherwise following the procedure as described in Example 5, the above-mentioned product is obtained; $n_D^{20} = 1.4810$.

| Analysis | % C | % H |
|---|---|---|
| calculated for C₁₃H₁₈O₂ | 75.69 | 8.80 |
| found | 76.00 | 8.70 |

Preparation of the allylbicyclo[2.2.1]hept-5-ene-2-carboxylic acid amides and diamides

Process A: via acid chloride

In the course of 30 minutes, a solution of 0.11 mole of monoamine (0.055 mole of diamine) in 25 ml of methylene chloride is added dropwise at 10° to 25° C. to a solution of 0.1 mole of allylbicyclo[2.2.1]hept-5-ene-2-carbonyl chloride and 0.12 mole of pyridine. The reaction mixture is stirred for 3 hours at 20° C., 200 ml of water are added, and the phases are separated. The organic phase is washed with 1N, HCl, aqueous soda solution and saturated sodium chloride solution, dried over sodium sulfate and filtered, and the solvent is distilled off by rotary evaporation at 60° C. The residue is stirred for 2 hours in vacuo at 120° to 160° C.

Process B: via methyl ester

In the course of 16 hours, a mixture of 0.105 mole of methyl allylbicyclo[2.2.1]hept-5-ene-2-carboxylate, 0.1 mole of an aliphatic amine (0.05 mole of diamine) and 50 mg of sodium ethylate is heated, with stirring, to 160° C. in a descending cooler. Subsequently, the pressure is reduced to 0.1 mm, and the mixture is stirred for 2 hours at 160° C.

EXAMPLE 7: Preparation of allylbicyclo[2.2.1]hept-5-ene-2-carboxylic acid amide

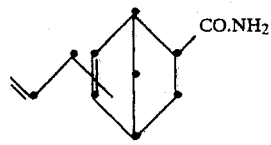

9.8 of allylbicyclo[2.2.1]hept-5-ene-2-carbonyl chloride are added dropwise over 10 minutes at 0° C. to 50 mol of 25% aqueous ammonia. The batch is stirred for 15 minutes at room temperature, and the water is decanted. The residue is dissolved in 50 ml of ether, washed with saturated soda solution and saturated sodium chloride solution, dried over sodium sulfate and concentrated, affording 6.5 g (73% of theory) of a white solid. For purification, the resultant solid is recrystalised from water; m.p.: 120°–122° C.

| Analysis | % C | % H | % N |
|---|---|---|---|
| calculated for C₁₁H₁₅NO | 74.54 | 8.53 | 7.90 |
| found | 73.41 | 8.41 | 7.75 |

EXAMPLE 8: Preparation of allylbicyclo[2.2.1]hept-5-ene-2-carboxylic acid N-methylamide

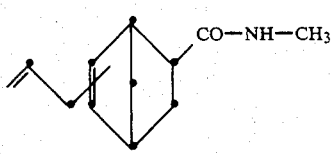

With cooling, 9.8 g of allylbicyclo[2.2.1]hept-5-ene-2-carbonyl chloride are added dropwise to 50 ml of a 40% aqueous methylamine solution. After 1 hour at 20° C., 100 ml of ether are added. The organic phase is separated, and working up is effected as described in Example 4, affording 8.0 g (84% of theory) of a yellow liquid. For the purpose of characterisation, a sample is distilled in a bulb tube; $n_D^{20} = 1.5160$; $\eta_{25} = 420$ mPas.

| | Analysis | | |
|---|---|---|---|
| | % C | % H | % N |
| calculated for $C_{12}H_{17}NO$ | 75.35 | 8.96 | 7.32 |
| found | 75.63 | 8.99 | 6.96 |

EXAMPLE 9: Preparation of allylbicyclo[2.2.1]hept-5-ene-2-carboxylic acid N-allylamide

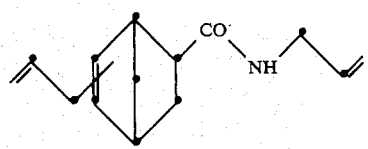

54 g of allylamine and 206 g of allylbicyclo[2.2.1]hept-5-ene-2-carbonyl chloride are reacted in accordance with process A. Distillation of the crude product affords 182 g (84%) of theory of amide in the form of a colourless liquid; b.p.: 122°–128° C. at 0.02 mm; $n_D^{20} = 1.5181$; $\eta n_{25} = 217.8$ mPas.

| | Analysis | | |
|---|---|---|---|
| | % C | % H | % N |
| calculated for $C_{14}H_{19}NO$ | 77.38 | 8.81 | 6.45 |
| found | 76.72 | 8.70 | 6.30 |

Polymerisation for 16 hours at 220° C. affords a solid with a glass transition temperature of 128.5° C.

EXAMPLE 10: Preparation of allylbicyclo[2.2.1]hept-5-ene-2-carboxylic acid N-cyclohexylamide

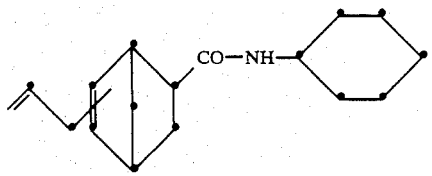

2.8 g of cyclohexylamine and 39.3 g of allylbicyclo[2.2.1]hept-5-ene-2-carbonyl chloride are reacted in accordance with process A, affording 40.7 g (78.9% of theory) of a reddish brown liquid resin; $\eta_{40} = 1128$ mPas.

| | Analysis | | |
|---|---|---|---|
| | % C | % H | % N |
| calculated for $C_{17}H_{24}NO$ | 79.02 | 9.36 | 5.46 |
| found | 78.49 | 9.60 | 5.40 |

Polymerisation for 10 hours at 200° c. affords a clear solid with a glass transition temperature of 72.5° C. The polymer is readily soluble in acetone, methylene chloride and tetrahydrofuran. Gel permeation chromatography (GPC) in tetrahydrofuran shows an $\overline{M}_n$ of 500 and an $\overline{M}_w$ of 1363.

EXAMPLE 11: Preparation of allylbicyclo[2.2.1]hept-5-en-2-carboxylic acid N-phenylamide

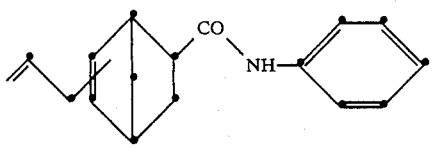

20.5 g of aniline and 39.3 g of allylbicyclo[2.2.1]hept-5-ene-2-carbonyl chloride are reacted in accordance with process A, affording 40.6 g (80.3% of theory) of a brown resin which is solid at room temperature and has a softening point of 66° C. The IR spectrum shows a band at 330 cm$^{-1}$ (—NH—) und at 1660 cm$^{-1}$ (>C=O). Average molecular weights of 308 ($\overline{M}_n$) and 311 ($\overline{M}_w$) respectively are measured by means of gel permeation chromatography (in THF).

| | Analysis | | |
|---|---|---|---|
| | % C | % H | % N |
| calculated for $C_{17}H_{19}NO$ | 80.60 | 7.56 | 5.53 |
| found | 80.45 | 7.58 | 5.42 |

Polymerisation for 10 hours at 200° C. affords a brown solid with a glass transition temperature of 94° C. The polymer is readily soluble in acetone, methylene chloride and tetrahydrofuran. Gel permeation chromatography (GPC) in tetrahydrofuran shows an $\overline{M}_n$ iof 640 and an $\overline{M}_w$ of 2439.

EXAMPLE 12: Preparation of allylbicyclo[2.2.1]hept-5-ene-2-carboxylic acid N-furfurylamide

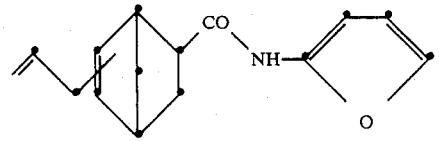

21.4 g of furfurylamine and 39.3 g of allylbicyclo[2.2.1]hept-5-ene-2-carbonyl chloride are reacted in accordance with process A, affording 38.1 g (73.8% of theory) of a reddish brown liquid resin; $\eta_{25} = 1287.2$ mPas.

| Analysis | | | |
|---|---|---|---|
| | % C | % H | % N |
| calculated for $C_{16}H_{20}NO_2$ | 74.39 | 7.80 | 5.42 |
| found | 74.45 | 7.43 | 5.35 |

Polymerisation for 10 hours at 200° C. affords a clear reddish brown solid with a glass transition temperature of 80° C.

EXAMPLE 13: Preparation of allylbicyclo[2.2.1]hept-5-ene-2-carboxylic acid N-(2-ethyl)hexylamide

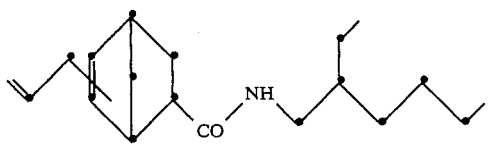

12.9 g of 2-ethylhexylamine and 21 g of methyl allylbicyclo[2.2.1]hept-5-ene-2-carboxylate are reacted in accordance with process B. Distillation of the crude product affords 20.6 g (71% of theory) of amide in the form of a slightly yellow liquid; $n_D^{20}=1.4390$ and $\eta_{25}=442$ mPas.

| Analysis | | | |
|---|---|---|---|
| | % C | % H | % N |
| calculated for $C_{19}H_{31}NO$ | 78.84 | 10.80 | 4.84 |
| found | 78.11 | 10.91 | 5.06 |

EXAMPLE 14: Preparation of allylbicyclo[2.2.1]hept-5-ene-2-carboxylic acid N-benzylamide

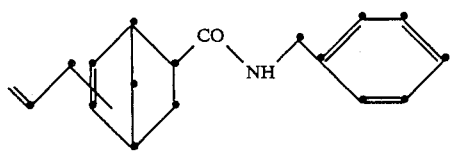

9.6 g of methyl allylbicyclo[2.2.1]hept-5-ene-2-carboxylate are mixed with 30 ml of benzylamine and 1 g of ammonium chloride, and the mixture is heated for 3 hours under reflux. After cooling, 100 ml of methylene chloride are added, and the reaction mixture is washed with 1N HCl, aqueous soda solution and saturated sodium chloride solution. The organic phase is dried and filtered, and the filtrate is concentrated, affording 3.8 g (73.4% of theory) of a red liquid resin. For the purpose of characterisation, a sample is distilled in a bomb tube. The distillate is a pale yellow oil; $\eta_{25}=310$ mPas.

| Analysis | | | |
|---|---|---|---|
| | % C | % H | % N |
| calculated for $C_{18}H_{21}NO$ | 80.86 | 7.92 | 5.24 |
| found | 80.89 | 7.97 | 5.59 |

EXAMPLE 15: Preparation of allylbicyclo[2.2.1]hept-5-ene-2-carboxylic acid N,N'-dimethylamide

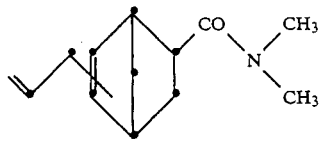

A solution of 19.6 g of allylbicyclo[2.2.1]hept-5-ene-2-carbonyl chloride in 200 ml of dioxane is added dropwise over 30 minutes at 20° C. to 40.9 g of dimethylamine (33% in ethanol). After stirring for 1 hour at 20° C., the turbid reaction mixture is filtered through a filter aid, and the dioxane is filtered off. The residue is taken up in 100 ml of methylene chloride, the resultant solution is washed with aqueous soda solution and saturated sodium chloride solution, dried over sodium sulfate and filtered, and the filtrate is concentrated, affording as residue 18.5 g (90.3% of theory) of a yellow liquid. The crude product is distilled at 140°–150° C./0.1 mm; $n_D^{20}=1.5124$.

| Analysis | | | |
|---|---|---|---|
| | % C | % H | % N |
| calculated for $C_{13}H_{19}NO$ | 76.06 | 9.33 | 6.82 |
| found | 76.59 | 9.37 | 6.40 |

EXAMPLE 16: Preparation of allylbicyclo[2.2.1]hept-5-ene-2-carboxylic acid N,N'-diallylamide

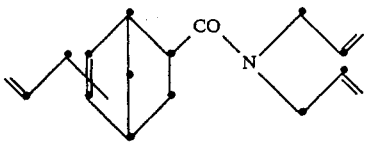

87.5 g of diallylamine and 175 g of allylbicyclo[2.2.1]hept-5-ene-2-carbonyl chloride are reacted in accordance with process A. Distillation of the crude product affords 173 g (75% of theory) of amide in the form of a slightly yellow liquid; $n_D^{20}=1.5142$ and $\eta_{25}=35.5$ mPas.

| Analysis | | | |
|---|---|---|---|
| | % C | % H | % N |
| calculated for $C_{17}H_{23}NO$ | 79.33 | 9.01 | 5.44 |
| found | 78.79 | 8.99 | 5.35 |

EXAMPLE 17: Preparation of allylbicyclo[2.2.1]hept-5-ene-2-carboxylic acid N,N'-diisobutylamide

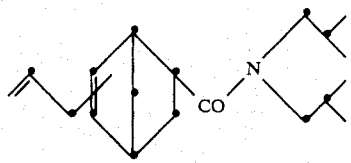

14.2 g of diisobutylamine and 19.6 g of allylbicyclo[2.2.1]hept-5-ene-2-carbonyl chloride are reacted in accordance with process A, affording 22.1 g (76.5% of theory) of a brown liquid resin. For the purpose of characterisation, a sample is distilled in a bomb tube. The distillate is a pale yellow liquid; $n_D^{20}=1.4915$ and $\eta_{25}=127$ mPas.

| | Analysis | | |
|---|---|---|---|
| | % C | % H | % N |
| calculated for $C_{19}H_{31}NO$ | 78.84 | 10.80 | 4.84 |
| found | 78.64 | 10.66 | 4.72 |

EXAMPLE 18: Preparation of allylbicyclo[2.2.1]hept-5-ene-2-carboxylic acid

N,N'-diphenylamide

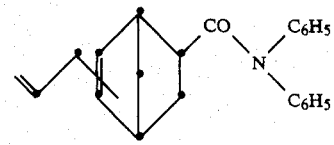

37.2 g of diphenylamine and 39.3 g of allylbicyclo[2.2.1]hept-5-ene-2-carbonyl chloride are reacted in accordance with process A, affording 50.6 g (77% of theory) of a reddish brown liquid resin; $\eta_{25}=4846$ mPas.

| | Analysis | | |
|---|---|---|---|
| | % C | % H | % N |
| calculated for $C_{23}H_{23}NO$ | 83.85 | 7.04 | 4.25 |
| found | 83.56 | 7.03 | 4.37 |

Polymerisation for 10 hours at 200° C. affords a clear reddish brown solid with a glass transition temperature of 58° C. Gel permeation chromatography (GPC) in tetrahydrofuran shows an $\overline{M}_n$ of 476 and an $\overline{M}_w$ of 1701.

EXAMPLE 19: Preparation of N,N'-ethylenebis(allylbicyclo[2.2.1]hept-5-ene-2-carboxylic acid amide)

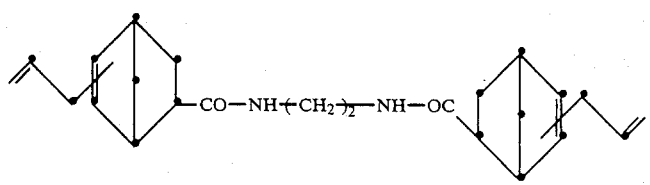

9.0 g of ethylenediamine and 58.9 g of allylbicyclo[2.2.1]hept-5-ene-2-carbonyl chloride are reacted in accordance with process A, affording 47.1 g (82.4% of theory) of a viscous, reddish brown resin; $\eta_{80}=2597$ mPas.

| | Analysis | | |
|---|---|---|---|
| | % C | % H | % N |
| calculated for $C_{24}H_{32}N_2O_2$ | 75.75 | 8.48 | 7.36 |
| found | 75.33 | 8.35 | 7.09 |

EXAMPLE 20: Preparation of N,N'-hexamethylenebis(allylbicyclo[2.2.1]hept-5-ene-2-carboxylic acid amide)

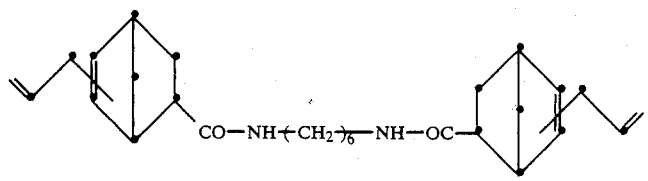

(A) 52.3 g of 1,6-diaminohexane and 172 g of allylbicyclo[2.2.1]hept-5-ene-2-carbonyl chloride are reacted in accordance with process A, affording 161.5 g (85% of theory) of a viscous red resin; $\eta_{80}=105$ mPas.

| | Analysis | | |
|---|---|---|---|
| | % C | % H | % N |
| calculated for $C_{28}H_{40}N_2O_2$ | 77.02 | 9.23 | 6.42 |
| found | 77.16 | 9.14 | 5.95 |

(B) 55.1 g of 1,6-diaminohexane and 191.7 g of methyl allylbicyclo[2.2.1]hept-5-ene-2-carboxylate are reacted in accordance with process B, affording 201 g (97% of theory) of an orange-coloured resin; $\eta_{80}=310$ mPas.

| Analysis | % C | % H | % N |
|---|---|---|---|
| calculated for C₂₈H₄₀N₂O₂ | 77.02 | 9.23 | 6.42 |
| found | 76.31 | 9.41 | 6.53 |

EXAMPLE 21: Preparation of bis[4-(allylbicyclo[2.2.1]hept-5-ene-2-carboxylic acid amidophenyl]methane

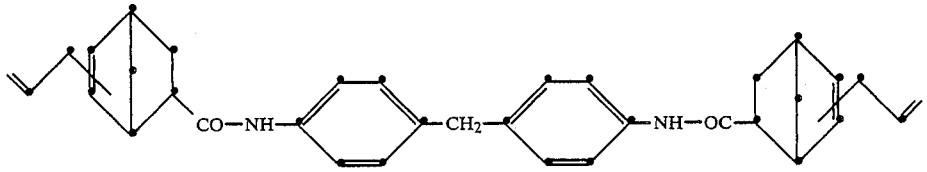

67 g of 4,4'-diaminodiphenylmethane and 127 g of allylbicyclo[2.2.1]hept-5-ene-2-carbonyl chloride are reacted in accordance with process A, affording 157 g (94% of theory) of a brown solid resin with a softening point of 66° C. By means of gel permeation chromatography (in THF), average molecular weights of 677 ($\overline{M}_n$) and 779 ($\overline{M}_w$) respectively are measured. The IR spectrum shows an absorption band at 3300 cm⁻¹ (—NH—) and 1660 cm⁻¹ (>C=O).

| Analysis | % C | % H | % N |
|---|---|---|---|
| calculated for C₃₅H₃₈N₂O₂ | 81.05 | 7.38 | 5.40 |
| found | 80.32 | 7.46 | 5.33 |

EXAMPLE 22: Preparation of N,N'-m-xylylenebis(allylbicyclo[2.2.1]hept-5-ene-2-carboxylic acid amide)

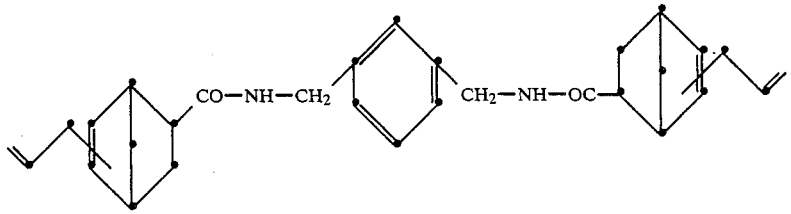

27 g of α,α'-diamino-m-xylene and 78,6 g of allylbicyclo[2.2.1]hept-5-ene-2-carbonyl chloride are reacted in accordance with process A, affording 73 g (80% of theory) of a reddish brown solid resin with a softening point of 106° C. and molecular weights of 530 ($\overline{M}_n$) and 1441 ($\overline{M}_w$) respectively, as measured by gel permeation chromatography (in THF). The IR spectrum shows an absorption band at 3300 cm⁻¹ (—NH—) and at 1650 cm⁻¹ (>C=O).

| Analysis | % C | % H | % N |
|---|---|---|---|
| calculated for C₃₀H₃₆N₂O₂ | 78.91 | 7.95 | 6.13 |
| found | 78.34 | 8.00 | 5.64 |

EXAMPLE 23: Preparation of N,N'-4,4'-(3,3'-dimethyl)diphenylbis(allylbicyclo[2.2.1]hept-5-ene-2-carboxylic acid amide)

29.0 g of o-tolidine and 58.9 g of allylbicyclo[2.2.1]hept-5-ene-2-carbonyl chloride are reacted in accordance with process A, affording 69.2 g (80% of theory) of a brown solid resin with a softening point of 82° C. and molecular weights of 739 ($\overline{M}_n$) and 2786 ($\overline{M}_w$) respectively, as determined by gel permeation chromatography (THF). The IR spectrum shows an absorption band at 3350 cm⁻¹ (—NH—) and at 1660 cm⁻¹ (>C=O).

| Analysis | % C | % H | % N |
|---|---|---|---|
| calculated for C₃₆H₃₉N₂O₂ | 81.32 | 7.39 | 5.27 |
| found | 81.10 | 7.62 | 4.80 |

EXAMPLE 24: Preparation of N,N'-diethylenebis(allylbicyclo[2.2.1]hept-5-ene-2-carboxylic acid amide)

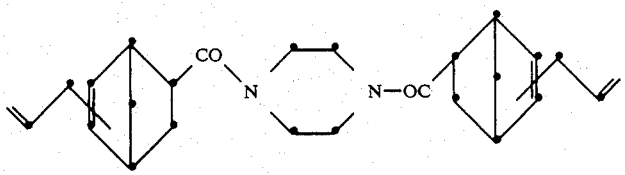

47.3 g of piperazine and 220 g of allylbicyclo[2.2.1-]hept-5-ene-2-carbonyl chloride are reacted in accordance with process A, affording 206 g (93% of theory) of a brownish red resin which is still liquid at room temperature. Molecular weights of 403 ($\overline{M}_n$) and 809 ($\overline{M}_w$) respectively are measured by means of gel permeation chromatography (THF). In the IR spectrum an absorption band occurs at 1650 cm$^{-1}$ (>C=O).

| | Analysis | | |
|---|---|---|---|
| | % C | % H | % N |
| calculated for $C_{26}H_{32}N_2O_2$ | 77.19 | 7.97 | 6.92 |
| found | 76.09 | 8.37 | 6.56 |

EXAMPLE 25: Preparation of bis[4-(diallylbicyclo[2.2.1]hept-5-ene-2-carboxylic acid amidophenyl]methane

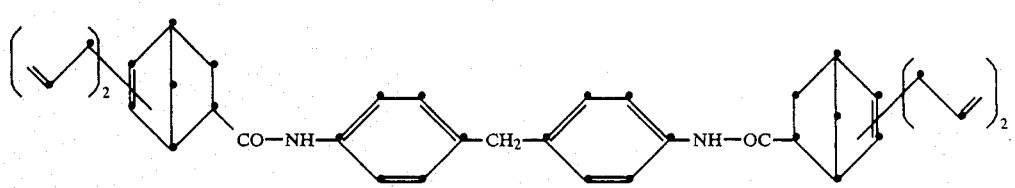

15.7 g of 4,4'-diaminodiphenylmethane and 38 g of diallylbicyclo[2.2.1]hept-5-ene-2-carbonyl chloride are reacted in accordance with process A, affording 35.3 g (74% of theory) of a brown solid resin with a softening point of 82° C. and molecular weights of 877 ($\overline{M}_n$) and 1501 ($\overline{M}_w$) respectively, as measured by gel permeation chromatography (THF). In the IR spectrum absorption band is found at 3310 cm$^{-1}$ (—NH—) and at 1660 cm$^{-1}$ (>C=O).

| | Analysis | | |
|---|---|---|---|
| | % C | % H | % N |
| calculated for $C_{41}H_{46}N_2O_2$ | 82.24 | 7.74 | 4.68 |
| found | 81.55 | 7.80 | 4.52 |

EXAMPLE 26: Preparation of bis[4-(methyllylmethylbicyclo[2.2.1]hept-5-ene-2-carboxylic acid amidophenyl)]methane

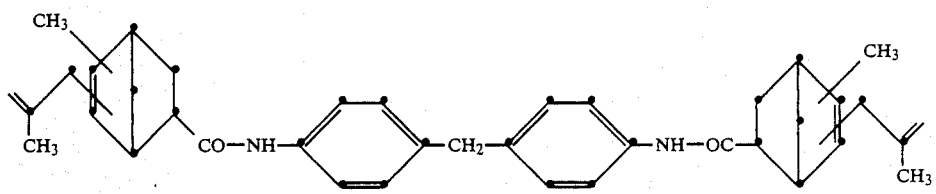

19.8 g of 4,4'-diaminodiphenylmethane and 44.9 g of methallylmethylbicyclo[2.2.1]hept-5-ene-2-carbonyl chloride are reacted in accordance with process A, affording 45.3 g (79% of theory) of a reddish brown solid resin with a softening point of 74° C. and molecular weights of 794 ($\overline{M}_n$) and 1114 ($\overline{M}_w$) respectively, as measured by gel permeation chromatography (THF). The IR spectrum shows an absorption band at 3310 cm$^{-1}$ (—NH—) and 1665 cm$^{-1}$ (>C=O).

| | Analysis | | |
|---|---|---|---|
| | % C | % H | % N |
| calculated for $C_{39}H_{46}N_2O_2$ | 81.49 | 8.07 | 4.57 |
| found | 80.85 | 8.00 | 4.58 |

EXAMPLE 27: Preparation of bis[4-(allylbicyclo[2.2.1]hept-5-ene-2-methyl-2-carboxylic acid amidophenyl)]methane

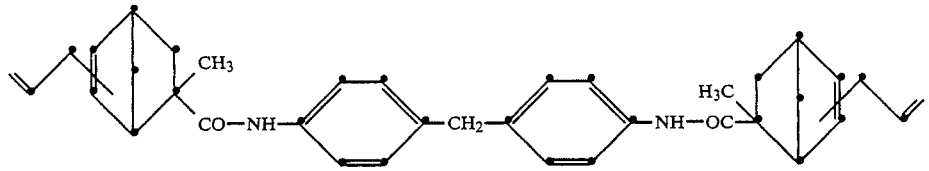

53.0 g of 4,4'-diaminodiphenylmethane and 113 g of allylbicyclo[2.2.1]hept-5-ene-2-methyl-2-carbonyl chloride are reacted in accordance with process A. A reddish brown solid resin with a softening point of 40° C. is isolated. Molecular weights of 674 ($\overline{M}_n$) and 714 ($\overline{M}_w$) respectively are determined by gel permeation chromatography (THF). In the IR spectrum an absorption band is present at 3340 cm$^{-1}$ (—NH—) and at 1660 cm$^{-1}$ (>C=O).

| Analysis | % C | % H | % N |
|---|---|---|---|
| calculated for C$_{37}$H$_{42}$N$_2$O$_2$ | 81.28 | 7.74 | 5.12 |
| found | 80.52 | 7.82 | 4.76 |

EXAMPLE 28: Preparation of the bisamide from 3-aminomethyl-3,5,5-trimethylcyclohexylamine and allylbicyclo[2.2.1]hept-5-ene-2-carboxylic acid

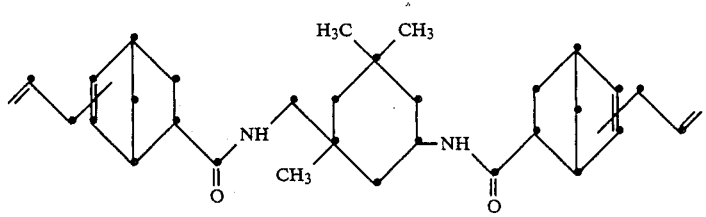

7.8 g of 3-aminomethyl-3,5,5-trimethylcyclohexylamine and 19.6 g of allylbicyclo[2.2.1]hept-5-ene-2-carbonyl chloride are reacted in accordance with process A, affording 19.4 g (79% of theory) of a light brown solid resin with a softening point of 63° C. Molecular weights of 628 ($\overline{M}_n$) and 1025 ($\overline{M}_w$) respectively are determined by gel permeation chromatography (THF). The IR spectrum shows an absorption band at 3310 cm$^{-1}$ (—NH—) and at 1650 cm$^{-1}$ (>C=O).

| Analysis | % C | % H | % N |
|---|---|---|---|
| calculated for C$_{32}$H$_{46}$N$_2$O$_2$ | 78.32 | 9.45 | 5.71 |
| found | 72.26 | 9.49 | 5.71 |

EXAMPLE 29: Preparation of N,N',N",N'''-triethylenetetra(allylbicyclo[2.2.1]hept-5-ene-2-methyl-2-carboxylic acid amide)

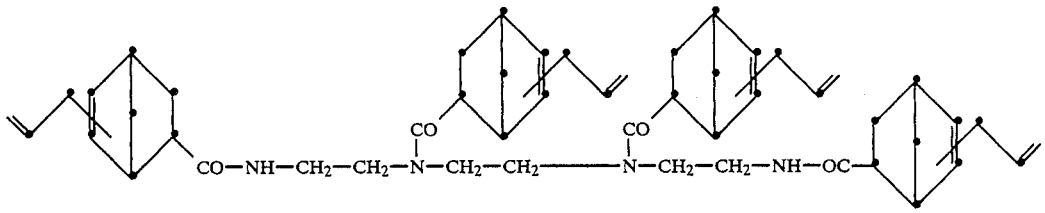

13.9 g of triethylenetetramine and 75.0 g of allylbicyclo[2.2.1]hept-5-ene-2-carbonyl chloride are reacted in accordance with process A, affording 54.0 g (72% of theory) of a reddish brown solid resin with a softening point of 82° C. and molecular weights of 898 ($\overline{M}_n$) and 1561 ($\overline{M}_w$) respectively, as determined by gel permeation chromatography (THF). The IR spectrum shows an absorption band at 3320 cm$^{-1}$ (—NH—) and 1640 cm$^{-1}$ (>C=O).

| Analysis | % C | % H | % N |
|---|---|---|---|
| calculated for C$_{50}$H$_{66}$N$_4$O$_4$ | 76.30 | 8.45 | 7.12 |
| found | 75.17 | 8.37 | 7.15 |

PREPARATION OF CROSSLINKED POLYMERS

The compounds of the present invention can be polymerised thermally. Crosslinked polymers with valuable physical properties are obtained.

EXAMPLES:

I. The diamide prepared according to Example 21 is poured as a hot, fluid resin into a steel mould (12×12×0.4 cm$^3$) and cured for 16 hours at 200° C. After cooling, sample rods are cut out of the clear reddish brown sheet. The following properties are measured:

| | |
|---|---|
| flexural strength acc. to ISO 178 (measurement at 23° C.) = | 79 N/mm$^2$ |
| impact strength acc. to VSM 77105 = | 38 8.3 kJ/m$^2$ |
| deflection temperature acc. to ISO 75 = | 226° C. |
| glass transition temperature T$_g$ (measured with TA 2000$^I$) = | 235° C. |
| water absorption (1 hour at 100° C.) = | 0.26% |
| 10% weight loss$^2$ = | 408° C. |

$^1$TA 2000 = differential thermoanalysis system TA 2000 of the company Mettler AG, Greifensee, CH.
$^2$Measurement made by heating a sample in the TA 2000; temperature determined at which 10% of the sample volatilise; rate of heating: 4° C./min. (in air).

When cementing aluminium sheets under the same curing conditions, with the two sheets to be cemented overlapping by 25×12 mm$^2$, the shear strength according to ISO 4587 (measured at room temperature) is 9.1 N/mm$^2$.

II. The diamide prepared according to Example 20A is poured into a steel mould (12×12×0.4 cm$^3$) and cured for 4 hours at 160° C. and for 10 hours at 200° C. The following properties are measured:

| | |
|---|---|
| flexural strength (ISO 178) = | 130 N/mm$^2$ |
| impact strength (VSM 77105) = | 11.9 kJ/m$^2$ |
| deflection temperature (ISO 75) = | 174° C. |
| glass transition temperature T$_g$ = | 187° C. |
| water absorption (1 hour at 100° C.) = | 0.41% |
| 10% weight loss = | 392° C. |
| shear strength (ISO 4587) = | 10.0 N/mm$^2$ |

III. The diamide prepared according to Example 20B is poured into a steel mould (8×6×0.4 cm$^3$) and cured for 16 hours at 200° C. and for 7 hours at 220° C.

| | |
|---|---|
| impact strength (VSM 77105) = | 9.5 kJ/m$^2$ |
| glass transition temperature T$_g$ = | 134° C. |
| 10% weight loss = | 423° C. |

IV. The diamide prepared according to Example 22 is poured into a steel mould (8×6×0.4 cm$^3$), and curing is effected as described in Example II.

| | |
|---|---|
| impact strength (VSM 77105) = | 7.3 kJ/m$^2$ |
| glass transition temperature T$_g$ = | 278° C. |
| shear strength (ISO 4587) = | 12.9 N/mm$^2$ |

V. The diamide prepared according to Example 24 is poured into a steel mould (12×12×0.4 cm$^3$), and curing is effected as described in Example II.

| | |
|---|---|
| flexural strength (ISO 178) = | 71 N/mm$^2$ |
| impact strength (VSM 77105) = | 4.6 kJ/m$^2$ |
| deflection temperature (ISO 75) = | >250° C. |
| glass transition temperature T$_g$ = | 256° C. |
| water absorption (1 hour at 100° C.) = | 0.56% |
| 10% weight loss = | 403° C. |

VI. The diamide prepared according to Example 25 is poured into a steel mould (8×6×0.4 cm$^3$), and curing is effected as described in Example II.

| | |
|---|---|
| impact strength (VSM 77105) = | 6.8 kJ/m$^2$ |
| glass transition temperature T$_g$ = | 265° C. |
| 10% weight loss = | 409° C. |

VII. The diamide prepared according to Example 26 is polymerised for 4 hours at 160° C., 2 hours at 180° C. and 10 hours at 200° C., yielding a clear red solid with a T$_g$ of 256° C.

VIII. The diamide prepared according to Example 27 is poured into a steel mould (8×6×0.4 cm$^3$), and curing is effected as described in Example II.

| | |
|---|---|
| impact strength (VSM 77105) = | 2.1 kJ/m$^2$ |
| glass transition temperature T$_g$ = | 213° C. |

IX. The diamide prepared according to Example 28 is poured into a steel mould (8×6×0.4 cm$^3$), and curing is effected as described in Example II.

| | |
|---|---|
| impact strength (VSM 77105) = | 6.1 kJ/m$^2$ |
| glass transition temperature T$_g$ = | 248° C. |
| 10% weight loss = | 408° C. |
| shear strength (ISO 4587) = | 6.7 N/mm$^2$ |

X. The diamide prepared according to Example 29 is poured into a steel mould (8×6×0.4 cm$^3$), and curing is effected as described in Example II.

| | |
|---|---|
| impact strength (VSM 77105) = | 5.2 kJ/m$^2$ |
| glass transition temperature T$_g$ = | 286° C. |
| 10% weight loss = | 402° C. |

XI. With stirring, 56 g of the diamide prepared according to Example 24 is dissolved in methylene chloride. The clear yellow solution is used as impregnating solution for the preparation of prepregs.

Prepreg Preparation: Lengths of fabric (245×16 cm) made of carbon fibres of the type G 814 NT manufactured by the company Brochier S. A. are drawn through the above-described impregnation solutions and then hung up to drip for 10 minutes. They are then laid out on a clothes-horse and dried for 8 minutes at 160° C. in a circulating air oven. The dried lengths of carbon fibre fabric are cut into pieces 13.5×14.5 cm in size. The resin content of the prepregs is determined by gravimetric measurement as being 49%.

Laminate Preparation: 11 layers of prepreg (13.5×14.5 cm) are each covered at both ends with a copper sheet and then wrapped in a poly(diphenyl oxide pyromellitimide) sheet (Kapton ®, manufactured by the company Du Pont). The prepregs are then placed in a press which has been preheated to 180° C. After a contact time of 2 minutes, a pressure of 907 kg is applied in the course of 2 minutes, thereby guaranteeing sufficient flow of the resin mixture. After 7 minutes, the pressure is increased over 3 minutes to 3628 kg, and this pressure is maintained for 1 hour at 180° C. The laminate thus obtained is cooled and then removed from the press at 100°–120° C. A laminate with a very good surface without visible interstices is obtained. The laminate is then postcured in a circulating air oven for 6 hours at 200° C. After curing, a high quality laminate with valuable mechanical and physical properties is obtained.

What is claimed is:
1. A compound of the formula:

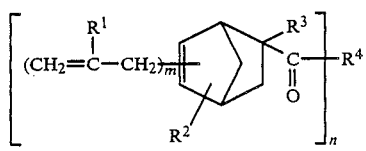

wherein
each of $R^1$, $R^2$, and $R^3$, independently of the other, is hydrogen or methyl;
m is an integer from 1 to 5;
n is an integer from 2 to 5; and
$R^4$ is the radical of an aliphatic, cycloaliphatic, aromatic, araliphatic, or heterocyclic polyamine having n primary or secondary amino groups, each of said n primary or secondary amino groups, after removal of a single active hydrogen atom, being bound to one of the depicted n carbonyl groups to form a carboxamido group.

2. A compound according to claim 1 wherein $R^1$ and $R^2$ are hydrogen and $R^3$ is methyl.

3. A compound according to claim 1 wherein $R^1$, $R^2$ and $R^3$ are hydrogen.

4. A compound according to claim 1 having the formula

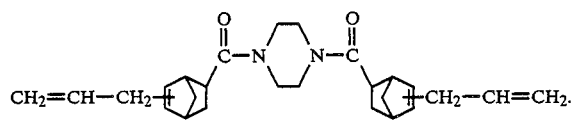

5. A compound according to claim 1 having the formula

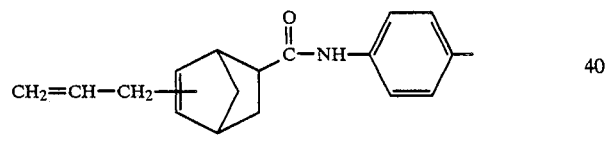

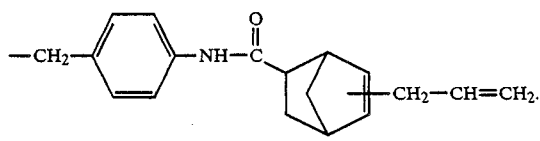

6. A compound of the formula

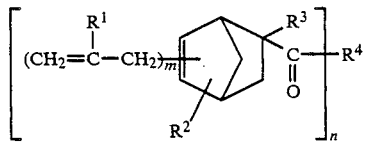

wherein
each of $R^1$, $R^2$, and $R^3$, independently of the other, is hydrogen or methyl;
m is an integer from 1 to 5;
n is an integer from 2 to 5; and
$R^4$ is the radical:

—NH—alkylene—NH,

-continued

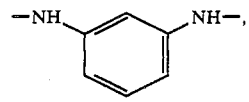

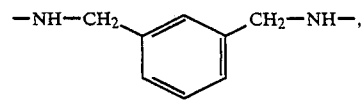

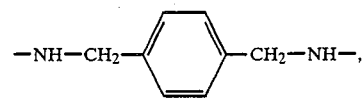

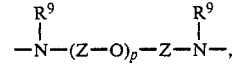

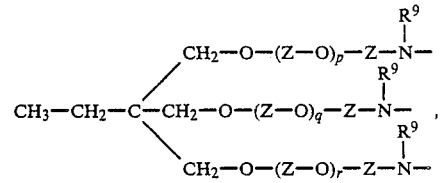

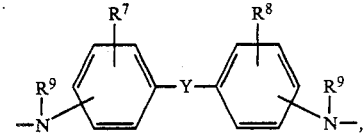

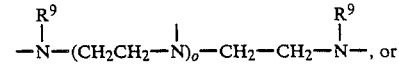

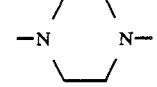

in which
each of $R^7$, $R^8$, and $R^9$, independently of the others, is hydrogen or alkyl of 1 to 5 carbon atoms;
Y is a carbon-carbon bond, —O—, —S—, —$SO_2$—, —CO—, —$CH_2$—, or —$C(CH_3)_2$—;
Z is —$CH_2CH_2$—, —$CH_2CH_2CH_2$—, or —$CH_2CH(CH_3)$—;
o is 0, 1, or 2; and
each of p, q, and r, independently of the others, is an integer of from 1 to 8.

7. A compound of the formula

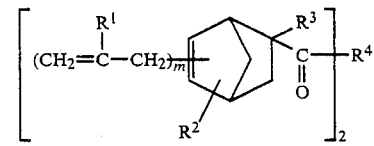

wherein
each of $R^1$, $R^2$, and $R^3$, independently of the other, is hydrogen or methyl;
m is 1 or 2; and
$R^4$ is the radical:
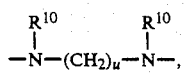
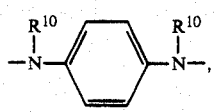
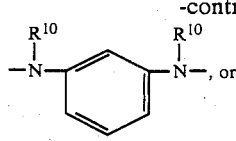
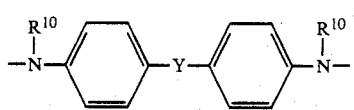
in which
$R^{10}$ is hydrogen, alkyl of 1 to 5 carbon atoms, or phenyl;
Y is —O—, —SO$_2$—, —CO—, or —CH$_2$—; and
u is an integer of from 2 to 12.
* * * * *